(12) United States Patent
Endo et al.

(10) Patent No.: US 8,273,919 B2
(45) Date of Patent: Sep. 25, 2012

(54) COMPOUND, SYNTHESIS METHOD THEREOF, AND OIL ADDITIVE

(75) Inventors: Akira Endo, Ibaraki (JP); Kimihiko Urata, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 340 days.

(21) Appl. No.: 12/738,909

(22) PCT Filed: Jan. 30, 2009

(86) PCT No.: PCT/JP2009/051667
§ 371 (c)(1),
(2), (4) Date: Apr. 20, 2010

(87) PCT Pub. No.: WO2009/096571
PCT Pub. Date: Aug. 6, 2009

(65) Prior Publication Data
US 2010/0210875 A1 Aug. 19, 2010

(30) Foreign Application Priority Data
Feb. 1, 2008 (JP) ................................. 2008-023258

(51) Int. Cl.
*C07C 231/02* (2006.01)
(52) U.S. Cl. ........... 564/142; 564/143; 564/155; 208/46
(58) Field of Classification Search .................. 564/142, 564/143, 155; 208/46
See application file for complete search history.

(56) References Cited

FOREIGN PATENT DOCUMENTS

| JP | S59-12708 | | 1/1984 |
|---|---|---|---|
| JP | 2-88635 | * | 3/1990 |
| JP | 5-1293 | * | 1/1993 |

* cited by examiner

*Primary Examiner* — Shailendra Kumar
(74) *Attorney, Agent, or Firm* — K. David Crockett, Esq.; Niky Economy Syrengelas, Esq.; Crockett & Crockett, PC (57) ABSTRACT

Problem: To provide a novel compound capable of preventing pyrolysis of fluorinated oils when it is used as an additive for the fluorinated oils.
Solution Means: A compound represented by Formula (1):

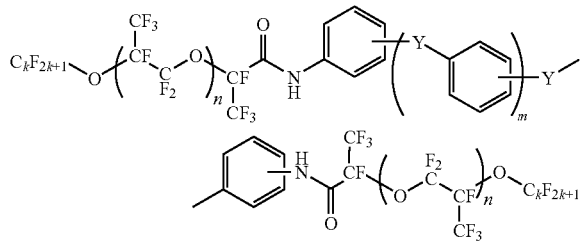

Formula (1)

wherein Y represents an oxygen atom (O), a sulfur atom (S), a CO group, a SO group, or a $SO_2$ group; k is an integer from 1 to 5; m is an integer from 1 to 10; and n is an integer of 1 or more; and wherein two substituents on each phenyl group may be in any of ortho-, meta-, and para-positions.

4 Claims, 4 Drawing Sheets

COMPOUND, SYNTHESIS METHOD THEREOF, AND OIL ADDITIVE

This application is a 371 of PCT/JP2009/051667, filed Jan. 30, 2009.

TECHNICAL FIELD

1. Field of the Invention

The present invention relates to a novel compound usable as an oil additive that is excellent at preventing pyrolysis of fluorinated oils; a synthesis method of the compound; and an oil additive.

2. Background of the Invention

Oil additives are generally added to oils for the purpose of adding or enhancing performance such as wear resistance, durability, heat resistance, rust resistance, etc.

Therefore, the development of oil additives is as important as the development of oils. In order to accomplish the above-mentioned object, research into novel compounds and synthesis methods thereof is ongoing.

The present inventors focused attention on additives for fluorinated oils among various oils, and continued research into various additives. Consequently, they found that pyrolysis of the polyether portions of fluorinated oils are responsible for the poor heat resistance of the fluorinated oils.

As a result of their continued research into techniques to prevent pyrolysis of fluorinated oils, the inventors found that a specific compound is capable of preventing pyrolysis of fluorinated oils when it is used as an oil additive.

Patent Document 1 discloses a defoaming agent of Formula (1), wherein m=0. This defoaming agent, however, has the problem of being poor at preventing pyrolysis of fluorinated oils when it is used as an additive for fluorinated oils.

Patent Document 1: Japanese Unexamined Patent Publication No. S59-12708

DISCLOSURE OF THE INVENTION

Problem to be Solved by the Invention

Accordingly, it is an object of the invention to provide a novel compound capable of preventing pyrolysis of fluorinated oils when it is used as an oil additive for the fluorinated oils.

It is another object of the invention to provide an oil additive capable of preventing pyrolysis of fluorinated oils.

It is still another object of the invention to provide a synthesis method of a novel compound produced using a compound that has a hydrogen fluoride trapping ability equal to that of sodium fluoride, and is less toxic than sodium fluoride.

Still other objects of the invention will become apparent from the following description.

Means for Solving the Problem

The above-mentioned objects will be solved by the inventions set forth below.

One new compound achieving these goals is a compound represented by Formula (1):

[Chem. 1]

Formula (1)

wherein Y represents an oxygen atom (O), a sulfur atom (S), a CO group, a SO group, or a $SO_2$ group; k is an integer from 1 to 5; m is an integer from 1 to 10; and n is an integer of 1 or more; and wherein two substituents on each phenyl group may be in any of ortho-, meta-, and para-positions.

Another new compound achieving these goals is the compound as defined in claim 1, wherein, in Formula (1), Y is an oxygen atom (O), and m is 1 or 2.

Another new compound achieving these goals is an oil additive represented by Formula (1) (hereinafter referred to as the "oil additive of the invention"):

[Chem. 2]

Formula (1)

wherein Y represents an oxygen atom (O), a sulfur atom (S), a CO group, a SO group, or a $SO_2$ group; k is an integer from 1 to 5; m is an integer from 1 to 10; and n is an integer of 1 or more; and wherein two substituents on each phenyl group may be in any of ortho-, meta-, and para-positions.

Another new compound achieving these goals is the oil additive as defined in, the preceding paragraphs wherein, in Formula (1), Y is an oxygen atom (O), and m is 1 or 2.

Another new compound achieving these goals is the oil additive as defined in the preceeding paragraphs, which is an additive for fluorinated oils. wherein, in Formula (1), Y is an oxygen atom (O), and m is 1 or 2.

Another new compound achieving these goals is a synthesis method comprising reacting an acid fluoride represented by Formula (2) with a compound having a diamino group represented by Formula (3) in pyridine solvent, thereby producing the compound of claim 1 represented by Formula (1):

[Chem. 3]

Formula (2)

wherein k is an integer from 1 to 5, and n is an integer of 1 or more; and

[Chem. 4]

Formula (3)

wherein Y represents an oxygen atom (O), a sulfur atom (S), a CO group, a SO group, or a $SO_2$ group; and m is an integer from 1 to 10; and wherein two substituents on each phenyl group may be in any of ortho-, meta-, and para-positions.

Another compound achieving these goals is the synthesis method as defined in the preceeding paragraphs, wherein the acid fluoride represented by Formula (2) is an acid fluoride represented by Formula (4):

[Chem. 5]

Formula (4)

wherein n is an integer of 1 or more.

Effects of the Invention

According to one aspect of the invention, there is provided a novel compound capable of preventing pyrolysis of fluorinated oils when it is used as an additive for the fluorinated oils.

According to another aspect of the invention, there is provided an oil additive that is capable of preventing pyrolysis of fluorinated oils when it is used as an additive for fluorinated oils.

According to still another aspect of the invention, there is provided a synthesis method of a novel compound produced using a material that has a hydrogen fluoride trapping ability equal to that of sodium fluoride, and is less toxic than sodium fluoride.

BEST MODE OF CARRYING OUT THE INVENTION

Embodiments of the invention are described below.
<Novel Compound>
The novel compound of the invention is a compound represented by Formula (1):

[Chem. 6]

Formula (1)

wherein Y represents an oxygen atom (O), a sulfur atom (S), a CO group, a SO group, or a SO$_2$ group, with an oxygen atom (O) being preferred.

In Formula (1), k is an integer from 1 to 5, and preferably 2 or 3.

In Formula (1), m is an integer from 1 to 10, preferably 1 to 5, and more preferably 1 or 2.

In Formula (1), n is an integer of 1 or more, and preferably 1 to 40.

The two substituents on each phenyl group may be in any of ortho-, meta-, and para-positions.

The synthesis method of the novel compound of the invention can be performed with reference to the detailed description given below. The novel compound can be suitably used as an additive for fluorinated oils. When the novel compound is added to a fluorinated oil, it is capable of preventing pyrolysis of the fluorinated oil.

<Novel Synthesis Method>

The synthesis method of the invention includes reacting an acid fluoride which is represented by Formula (2) below, and is preferably represented by Formula (4) below, with a compound having a diamino group represented by Formula (3) below, in pyridine solvent, thereby producing the compound of claim 1 represented by Formula (1).

[Chem. 7]

Formula (2)

wherein k is an integer from 1 to 5, and n is an integer of 1 or more.

[Chem. 8]

Formula (4)

wherein n is an integer of 1 or more, and preferably 1 to 40.

[Chem. 9]

Formula (3)

wherein Y represents an oxygen atom (O), a sulfur atom (S), a CO group, a SO group, or a SO$_2$ group, with an oxygen atom (O) being preferred.

In Formula (3), m is an integer from 1 to 10, preferably 1 to 5, and more preferably 1 or 2.

The two substituents on each phenyl group may be in any of ortho-, meta-, and para-positions.

The synthesis method of the invention is performed in pyridine solvent. The method uses the material (pyridine) that has a hydrogen fluoride trapping ability equal to that of sodium fluoride, and is less toxic than sodium fluoride, and hence, is free of any problem encountered with sodium fluoride.

The toxicity and characteristics of pyridine are as follows.
Oral toxicity in rats: LD 50, 890 mg/kg
Liquid at room temperature (melting point: −42° C., boiling point: 115.5° C.)

It is not necessary that pyridine, which is the solvent of the invention, be used alone. In order to improve the solubility of the starting compounds and reaction product, pyridine may be used together with other organic solvents.

Examples of the compound having a diamino group represented by Formula (3) include 1,4-bis(4-1,4-Bis(4-aminophenoxy)benzene is commercially available, such as CAS No. 10526-07-5, 2479-46-1, and 3491-12-1.

The compound having a diamino group may also be an aromatic polyether wherein m=2 or more, or may be a compound wherein the atom O (oxygen atom) of each ether linkage is substituted by CO, S, SO, or SO$_2$ (e.g., CAS No. 141699-34-5, 60191-34-6, or 17619-11-3).

The above-described synthesis method is a method for the synthesis of a compound represented by Formula (1), wherein k is 3; however, a compound can be similarly produced using an acid fluoride wherein k represents a different integer. Also in this case, it is important to use pyridine solvent.

It should be noted here that Patent Document 1 (Japanese Unexamined Patent Publication No. S59-12708) discloses a synthesis example of a fluorinated ether aromatic diamide compound as a defoaming agent. Specifically, a compound having a diamide group (hereinafter, the "diamide") is produced by reacting an acid fluoride of a poly(perfluoroether) compound with p,p'-diamino diphenyl ether, using sodium fluoride. Reference Example 13 of Patent Document 1 discloses an example in which the diamide I shown below is produced using p,p'-diamino diphenyl ether having the structure shown below:

[Chem. 10]

(p,p'-diamino diphenyl ether)

[Chem. 11]

(diamide I)

Also in reactions using acid fluorides other than that disclosed in Patent Document 1, hazardous hydrogen fluoride is produced as a by-product. For this reason, sodium fluoride is frequently used as a trapping agent for hydrogen fluoride.

Sodium fluoride, however, is an acute toxic substance (oral toxicity in rats: LD 50, 180 mg/kg). Further, due to its powdery form, sodium fluoride easily flies or floats up, and may cause permanent damage when it is attached to the skin or mucosa. Therefore, sodium fluoride has problems with handling.

Exemplary compounds of the novel compound of the invention or novel compound produced by the novel synthesis method of the invention include:

a compound of Formula (1), wherein k=3, m=1, n=1, Y is an oxygen atom, and the substituents are in the para-position (Exemplary Compound 1-1);

a compound of Formula (1), wherein k=3, m=1, n=11, Y is an oxygen atom, and the substituents are in the para-position (Exemplary Compound 1-2);

a compound of Formula (1), wherein k=3, m=1, n=40, Y is an oxygen atom, and the substituents are in the para-position (Exemplary Compound 1-3); and a compound of Formula (1), wherein k=3, m=2, n=1, Y is an oxygen atom, and the substituents are in the para-position (Exemplary Compound 1-4).

<Oil Additive>

While the oil additive of the invention can be added to various base oils (oils), it is preferably added to fluorinated oils to prevent pyrolysis of the fluorinated oils.

The fluorinated oil used is not particularly limited, and may be any known fluorinated oil.

In Formula (1), the value of n affects the affinity and solubility of the compound with the base oil. Where n=0, the composition represented by Formula (1) does not dissolve into the base oil when it is added to the oil.

The value of m affects the prevention of decomposition of the polyether (ether linkage) of the fluorinated oil. Where m=0, the polyether (ether linkage) of the fluorinated oil decomposes when the oil is used at high temperatures (e.g., from 400 to 430° C.). That is, where m=0, the fluorinated oil undergoes pyrolysis.

Patent Document 1 (Japanese Unexamined Patent Publication No. S59-12708) discloses a defoaming agent wherein m=0. However, even if this defoaming agent is used as an additive for fluorinated oils, it has the problem of being poor at preventing pyrolysis of fluorinated oils, and hence, cannot exhibit the effects of the invention.

The proportion of the oil additive of the invention added to a fluorinated oil is preferably 0.1 to 15 parts by weight, and more preferably 0.5 to 10 parts by weight, per 100 parts by weight of the base oil.

EXAMPLES

The invention will be described in greater detail below based on the following Examples; however, the invention is not limited to these Examples.

Synthesis Example 1

Synthesis of Exemplary Compound 1-1 (of Formula (1), wherein k=3, m=1, n=1, Y is an oxygen atom, and the substituents are in the para-position)

29.5 g of 1,4-bis(4-aminophenoxy)benzene was dissolved in 200 mL of pyridine; 124 g of an acid fluoride (n=1) was slowly added dropwise to the solution on an ice bath, and the mixture was stirred overnight at 0° C. to room temperature.

MeOH (50 mL) was added and stirred; subsequently, the mixture was neutralized with saturated $NaHCO_3$-aq.

The neutralized mixture was then extracted with AK-225 (mixture of $CF_3CF_2CHCl_2$ and $CClF_2CF_2CHClF$), and washed with saturated NaCl-aq.

The AK-255 was distilled off using an evaporator, thus yielding a yellow powder (124.8 g, 99.1%).

The structure of the obtained yellow powder was confirmed using $^1$H-NMR and $^{19}$F-NMR.

(Results)

$^1$H-NMR (Pyridine-$d_5$)

7.158 (4H, s, —O-Ph-O—)

7.16 to 7.19 (4H, m, NH-Ph-O-Ph-O-Ph-NH)

7.90 to 7.95 (4H, m, NH-Ph-O-Ph-O-Ph-NH)

12.707, 12.726 (2H, 2s, NH×2)

Ph in the range of 7.16-7.19 and in the range of 7.90-7.95 is represented by either Chem. 12 or 13:

[Chem. 12]

[Chem. 13]

$^{19}$F-NMR (Pyridine-$d_5$)

−145.3 (2F, m, —OCF(CF$_3$)CF$_2$—O— ×2)

−131.1 (2F, m, —O—CF(CF$_3$)CO—NH— ×2)

−129.79, −129.76 (4F, 2s, CF$_3$CF$_2$CF$_2$— ×2)

−83 to −80 (26F*, m, CF$_3$CF$_2$CF$_2$— ×2, —OCF(CF$_3$)CF$_2$—O— ×2, —O—CF(CF$_3$)CO—NH— ×2)

*Peaks are overlapping and cannot be resolved.

Synthesis Example 2

Synthesis of Exemplary Compound 1-2 (of Formula (1), wherein k=3, m=1, n=11, Y is an oxygen atom, and the substituents are in the para-position)

10.1 g of 1,4-bis(4-aminophenoxy)benzene was dissolved in a mixed solvent of 100 mL of pyridine and AK-225 (100 mL), and 209.0 g of an acid fluoride (n=11) was slowly added dropwise to the solution at room temperature. The mixture was stirred overnight at room temperature to 40° C.

MeOH (50 mL) was added and stirred; subsequently, the mixture was neutralized with saturated $NaHCO_3$-aq.

The neutralized mixture was then extracted with AK-225, and washed with saturated NaCl-aq.

The AK-255 was subsequently distilled off using an evaporator, thus yielding a pale yellow, high-viscosity liquid (173.9 g, 96.3%). The structure of the obtained pale yellow liquid was confirmed using $^1$H-NMR and $^{19}$F-NMR.

(Results)
$^1$H-NMR (Perfluorobenzene/Pyridine-$d_5$=3/1)
6.93 (4H, d, J=8.8 Hz, NH-Ph-O-Ph-O-Ph-NH)
6.9953 (4H, s, —O-Ph-O—)
7.69 (4H, d, J=8.6 Hz, NH-Ph-O-Ph-O-Ph-NH)
11.9518 (2H, s, NH×2)

As in Synthesis Example 1, Ph at 6.93 and 7.69 is represented by either Chem. 12 or 13 shown above.

hu 19F-NMR (Perfluorobenzene/Pyridine-$d_5$=3/1)
−143.1 (22F, m, —O—$CF(CF_3)CF_2$—O— ×11×2)
−128 to −130 (6F, m, —O—$CF(CF_3)$CO—NH— ×2, $CF_3CF_2CF_2$— ×2)
−78 to −81
(126F*, m, $CF_3CF_2CF_2$— ×2, —$OCF(CF_3)CF_2$—O— ×11×2, —O—$CF(CF_3)$CO—NH— ×2)
*Peaks are overlapping and cannot be resolved.

Synthesis Example 3

Synthesis of Exemplary Compound 1-3 (of Formula (1), wherein k=3, m=1, n=40, Y is an oxygen atom, and the substituents are in the para-position)

2.0 g of 1,4-bis(4-aminophenoxy)benzene was dissolved in a mixed solvent of 100 mL of pyridine and AK-225 (100 mL), and 101.0 g of an acid fluoride (n=40) was slowly added dropwise to the solution at room temperature. The mixture was stirred overnight at room temperature to 40° C.

MeOH (50 mL) was added and stirred; subsequently, the mixture was neutralized with saturated $NaHCO_3$-aq.

The neutralized mixture was then extracted with AK-225, and washed with saturated NaCl-aq.

The AK-255 was subsequently distilled off using an evaporator, thus yielding a pale yellow, high-viscosity liquid (97.6 g, 99.6%). The structure of the obtained pale yellow liquid was confirmed using $^1$H-NMR and $^{19}$F-NMR.

(Results)
$^1$H-NMR (neat)
6.9 (8H*, m, NH-Ph-O-Ph-O-Ph-NH)
7.3 (4H, m, NH-Ph-O-Ph-O-Ph-NH)
8.0 (2H, br.s, NH×2)
*Peaks are overlapping and cannot be resolved.

As in Synthesis Example 1, Ph bonded to NH at 6.9 and 7.3 is represented by either Chem. 12 or 13 shown above.

$^{19}$F-NMR (neat)
−142 (80F, m, —OCF ($CF_3)CF_2$—O— ×40×2)
−128 to −130 (6F, m, —O—$CF(CF_3)$CO—NH— ×2, $CF_3CF_2CF_2$— ×2)
−77 to −81 (416F, m, $CF_3CF_2CF_2$— ×2, —OCF ($CF_3)CF_2$—O— ×40×2, —O—$CF(CF_3)$CO—NH— ×2)

Synthesis Example 4

Synthesis of Exemplary Compound 1-4 (of Formula (1), wherein k=3, m=2, n=1, Y is an oxygen atom, and the substituents are in the para-position)

Bis[4-(4-aminophenoxy)phenyl]ether (25.2 g; a compound of Formula (3), wherein m=2, Y is an oxygen atom, and the substituents are in the para-position; CAS No. 13080-88-1) was dissolved in 200 mL of pyridine; 79 g of an acid fluoride (n=1) was slowly added dropwise to the solution on an ice bath, and the mixture was stirred overnight at 0° C. to room temperature.

MeOH (50 mL) was added and stirred; subsequently, the mixture was neutralized with saturated $NaHCO_3$-aq.

The neutralized mixture was then extracted with AK-225 (mixture of $CF_3CF_2CHCl_2$ and $CClF_2CF_2CHClF$), and washed with saturated NaCl-aq.

The AK-255 was subsequently distilled off using an evaporator, thus yielding a pale yellow, high-viscosity liquid (86.4 g, 98.3%). The structure of the obtained pale yellow, high-viscosity liquid was confirmed using $^1$H-NMR and $^{19}$F-NMR.

(Results)
$^1$H-NMR (Pyridine-$d_5$)
7.159 (8H*, s, NH-Ph-O-Ph-O-Ph-O-Ph-NH)
7.16 to 7.20 (4H, m, NH-Ph-O-Ph-O-Ph-O-Ph-NH)
7.91 to 7.94 (4H, m, NH-Ph-O-Ph-O-Ph-O-Ph-NH)
12.705, 12.727 (2H, 2s, NH×2)
*Peaks are overlapping and cannot be resolved.

Ph in the range of 7.16-7.20 and in the range of 7.91-7.94 is represented by either Chem. 12 or 13 shown above.

$^{19}$F-NMR (Pyridine-$d_5$)
−145.4 (2F, m, —$OCF(CF_3)CF_2$—O— ×2)
−131.1 (2F, m, —O—$CF(CF_3)$CO—NH— ×2)
−129.78, −129.75 (4F, 2s, $CF_3CF_2CF_2$— ×2)
−84 to −79 (26F*, m, $CF_3CF_2CF_2$— ×2, —$OCF(CF_3)CF_2$—O— ×2, —O—CF ($CF_3$)CO—NH— ×2)
*Peaks are overlapping and cannot be resolved.

Comparative Example 1

Example wherein the additive of the invention is not added.

Figure 1:
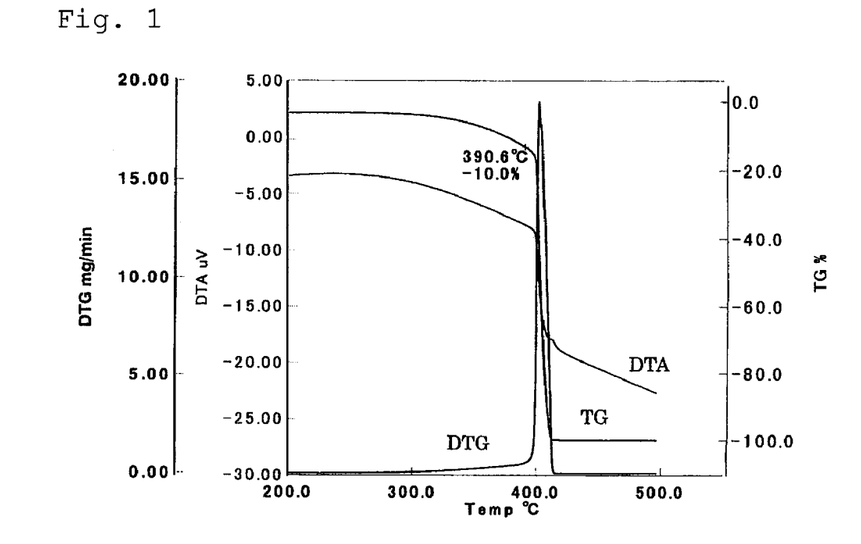
FIG. 1 is a graph showing the results obtained in Comparative Example 1.

The oil "Fomblin M30" was subjected to thermal analysis (TG/DTA). The results are shown in FIG. 1.

The results show that a weight change of −10% (TG %) was observed at a temperature of 390.6° C.; an abrupt change was observed at around 400° C.; and a change of −100% was reached at 410° C. (i.e., all the sample was evaporated, or presumed to be decomposed and evaporated).

<Measurement Conditions>
Quantity of sample: 10 mg
Heating rate: 20° C./min
Initial temperature: 25° C.
Maximum temperature: 500° C.
Atmospheric gas: none Example 1

Figure 2:
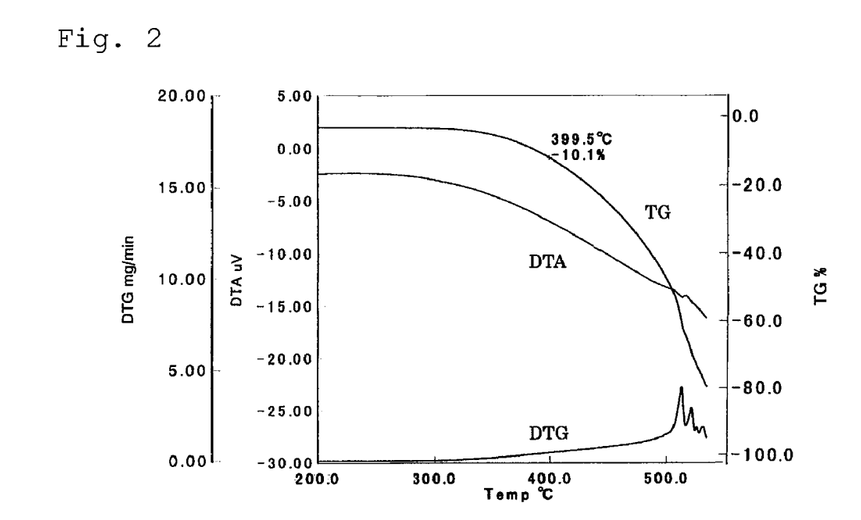
FIG. 2 is a graph showing the results obtained in Example 1

1 wt % of the product obtained in Synthesis Example 2 was added to the oil "Fomblin M30", and the resulting oil was subjected to thermal analysis under the same conditions as those in Comparative Example 1. The results are shown in FIG. 2.

The results show that the change at 400° C. or less was equivalent to that observed in the oil not containing the additive of the invention (399.5° C., −10.1%).

However, no abrupt changes were observed even after the temperature exceeded 400° C.; a change of slightly less than −30% was observed at 450° C., and a change of −50% was observed at 500° C. The oil was confirmed to exhibit improved heat resistance, compared with the oil not containing the additive of the invention.

Example 2

Figure 3:
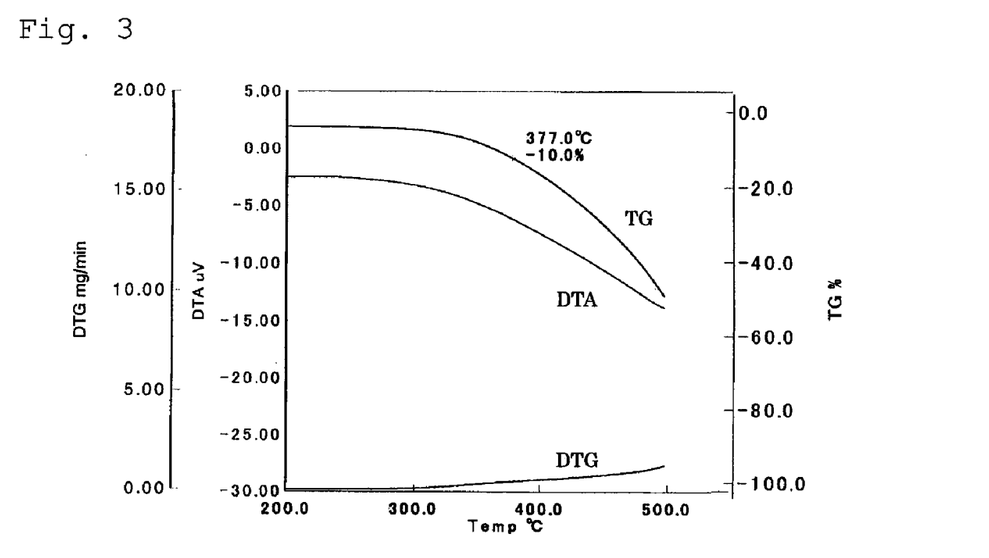
FIG. 3 is a graph showing the results obtained in Example 2.

3 wt % of the product obtained in Synthesis Example 2 was added to the oil "Fomblin M30", and the resulting oil was subjected to thermal analysis under the same conditions as those in Comparative Example 1. The results are shown in FIG. 3.

The results show that, as in Example 1, a change of slightly less than −30% was observed at 450° C., and a change of −50% was observed at 500° C.

The oil was confirmed to exhibit improved heat resistance, compared with the oil of Comparative Example 1 not containing the additive of the invention.

Example 3

Figure 4:
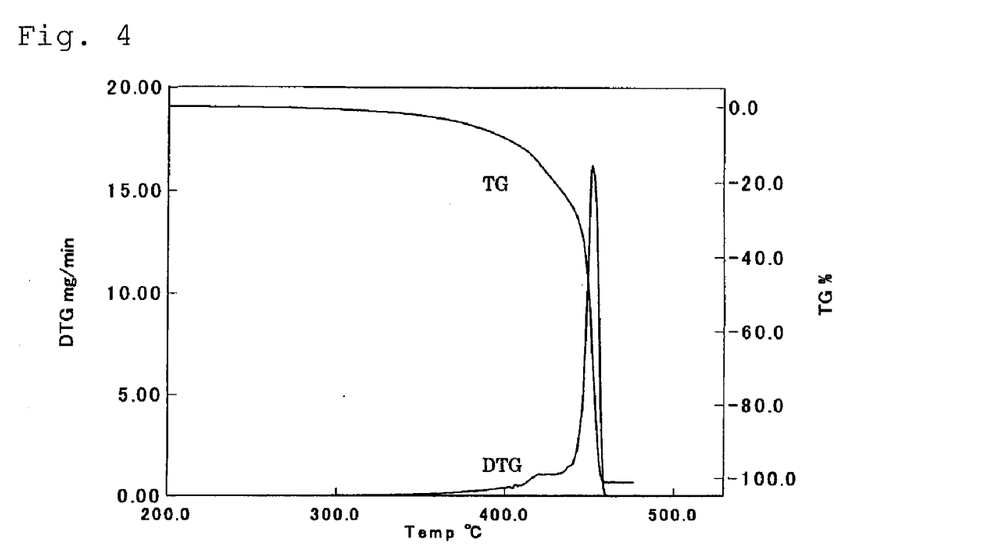
FIG. 4 is a graph showing the results obtained in Example 3.

An oil was prepared in the same manner as in Example 1, except that the compound of Synthesis Example 1 was used instead of the compound of Synthesis Example 2, and the resulting oil was subjected to thermal analysis under the same conditions as those in Comparative Example 1. The results are shown in FIG. 4.

An abrupt change was observed at around 400° C., and a change of −100% was reached at 460° C.

Example 4

Figure 5:
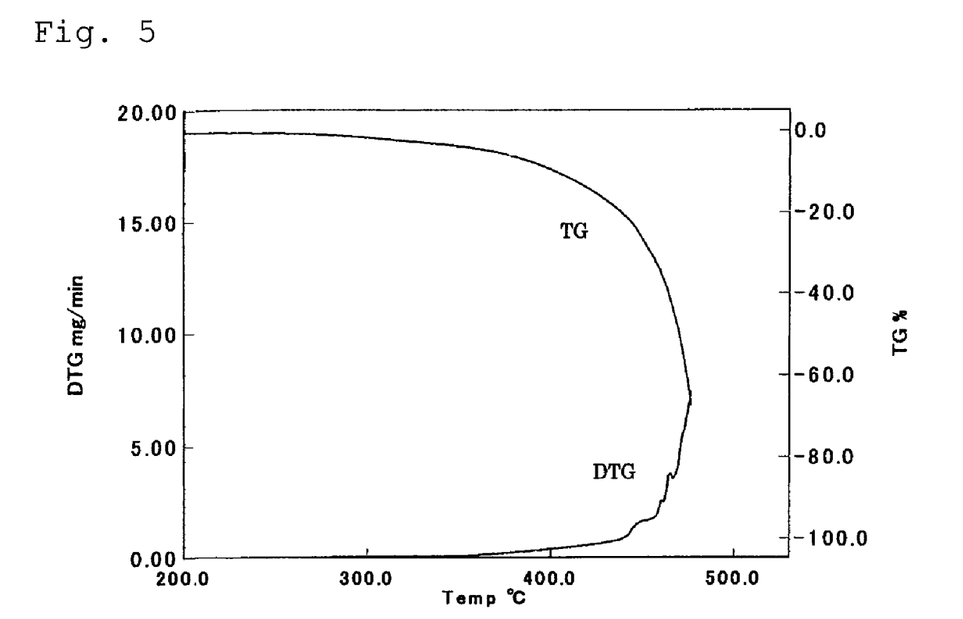
FIG. 5 is a graph showing the results obtained in Example 4.

An oil was prepared in the same manner as in Example 2, except that the compound of Synthesis Example 1 was used instead of the compound of Synthesis Example 2, and the resulting oil was subjected to thermal analysis under the same conditions as those in Comparative Example 1. The results are shown in FIG. 5.

An abrupt change was observed at around 400° C., and a change of −50% was reached at 470° C.

Comparative Example 2

Figure 6:
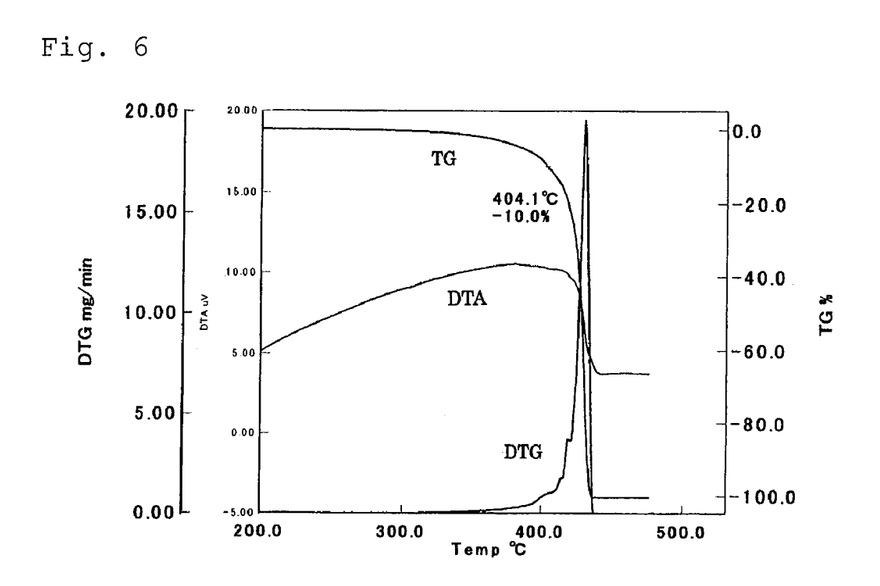
FIG. 6 is a graph showing the results obtained in Comparative Example 2.

1 wt % of a product of Formula (1), wherein k=3, m=0, n=1, and Y=an oxygen atom in the para-position, was added to the oil "Fomblin M30", and the resulting oil was subjected to thermal analysis under the same conditions as in Comparative Example 1. The results are shown in FIG. 6.

An abrupt change was observed at around 400° C., and a change of −100% was reached at 430° C.

The invention claimed is:

1. A synthesis method comprising reacting an acid fluoride represented by Formula (2) with a compound having a diamino group represented by Formula (3) in pyridine solvent, thereby producing the compound represented by Formula (1):

Formula (2)

wherein k is an integer from 1 to 5, and n is an integer of 1 or more;

Formula (3)

wherein Y represents an oxygen atom (O), a sulfur atom (S), a CO group, a SO group, or a $SO_2$ group; and m is an integer from 1 to 10; and wherein two substituents on each phenyl group may be in any of ortho-, meta-, and para-positions; and Formula (1)

wherein Y represents an oxygen atom (O), a sulfur atom (S), a CO group, a SO group, or a $SO_2$ group; k is an integer from 1 to 5; m is an integer from 1 to 10; and n is an integer of 1 or more; and wherein two substituents on each phenyl group may be in any of ortho-, meta-, and para-positions.

2. The synthesis method according to claim 1, wherein the acid fluoride represented by Formula (2) is an acid fluoride represented by Formula (4):

Formula (4)

wherein n is an integer of 1 or more.

3. An oil additive excellent at preventing pyrolysis of fluorinated oils, which is an additive for fluorinated oils represented by Formula (1):

Formula (1)

wherein Y represents an oxygen atom (O), a sulfur atom (S), a CO group, a SO group, or a $SO_2$ group; k is an integer from 1 to 5; m is an integer from 1 to 10; and n is an integer of 1 or more; and wherein two substituents on each phenyl group may be in any of ortho-, meta-, and para-positions.

4. The oil additive according to claim 3, wherein, in Formula (1), Y is an oxygen atom (O), and m is 1 or 2.

* * * * *